United States Patent [19]

Chapelon et al.

[11] Patent Number: 5,316,000
[45] Date of Patent: May 31, 1994

[54] USE OF AT LEAST ONE COMPOSITE PIEZOELECTRIC TRANSDUCER IN THE MANUFACTURE OF AN ULTRASONIC THERAPY APPARATUS FOR APPLYING THERAPY, IN A BODY ZONE, IN PARTICULAR TO CONCRETIONS, TO TISSUE, OR TO BONES, OF A LIVING BEING AND METHOD OF ULTRASONIC THERAPY

[75] Inventors: Jean-Yves Chapelon, Villeurbanne; Dominique Cathignol, Genas; Emmanuel Blanc, St Genis Laval, all of France

[73] Assignees: Technomed International (Societe Anonyme); Institut National de Recherche Meicale (Establissement Public), both of Paris, France

[21] Appl. No.: 823,306

[22] Filed: Jan. 21, 1992

Related U.S. Application Data

[63] Continuation-in-part of Ser. No. 795,197, Nov. 19, 1991.

[30] Foreign Application Priority Data

Mar. 5, 1991 [FR] France .................... 91 02620
Jul. 19, 1991 [FR] France .................... 91 09197

[51] Int. Cl.⁵ .................................... A61B 8/00
[52] U.S. Cl. ...................... 128/660.03; 128/24 AA; 128/24 EL; 607/97; 310/334
[58] Field of Search ........ 128/660.03, 24 AA, 24 EL; 310/334, 335; 607/97

[56] References Cited

U.S. PATENT DOCUMENTS

| | | | |
|---|---|---|---|
| 4,398,116 | 8/1983 | Lewis | 310/334 |
| 4,523,471 | 6/1985 | Lee | 310/334 |
| 4,534,221 | 8/1985 | Fife et al. | 128/661.001 |
| 4,628,223 | 12/1986 | Takeuchi et al. | 310/334 X |
| 4,640,291 | 2/1987 | 't Hoen | 310/334 |
| 4,888,746 | 12/1989 | Wurster et al. | 128/24 EL |
| 4,960,107 | 10/1990 | Aida et al. | 606/128 |
| 4,961,176 | 10/1990 | Tanaka et al. | 128/660.001 |
| 5,015,929 | 5/1991 | Cathignol et al. | 310/334 X |
| 5,122,993 | 6/1992 | Hikita et al. | 128/662.003 |
| 5,164,920 | 11/1992 | Bast et al. | 128/24 AA |

FOREIGN PATENT DOCUMENTS 0137529 4/1985 European Pat. Off. ..... G10K 11/34
0326701 8/1989 European Pat. Off. ..... A61B 17/22

OTHER PUBLICATIONS

IEEE 1989 Ultrasonics Symposium, Oct. 3-6, 1989 pp. 755-766.

Primary Examiner—Lee S. Cohen
Assistant Examiner—Brian L. Casler
Attorney, Agent, or Firm—Cohen, Pontani, Lieberman, Pavane

[57] ABSTRACT

The invention relates to a composite piezoelectric transducer for making an acoustic or an ultrasonic therapeutic apparatus. The transducer may be a single large-size transducer or it may be a multi-transducer device and it advantageously emits ultrasonic waves that are focused on a focal point.

23 Claims, 5 Drawing Sheets

USE OF AT LEAST ONE COMPOSITE PIEZOELECTRIC TRANSDUCER IN THE MANUFACTURE OF AN ULTRASONIC THERAPY APPARATUS FOR APPLYING THERAPY, IN A BODY ZONE, IN PARTICULAR TO CONCRETIONS, TO TISSUE, OR TO BONES, OF A LIVING BEING AND METHOD OF ULTRASONIC THERAPY

This application is a continuation-in-part application of U.S. application Ser. No. 07/795,197 filed on Nov. 19, 1991.

The invention relates essentially to the use of at least one composite piezoelectric transducer in the manufacture of an ultrasonic therapy apparatuses for applying therapy in a body zone, in particular to concretions, to tissue, or to bones, of a living being and a method of ultrasonic therapy.

BACKGROUND OF THE INVENTION

The existence of composite piezoelectric transducers is quite recent. Composite piezoelectric ceramics are constituted by conventional PZT (zirconate/titanate) type piezoelectric elements included in a polymer matrix. For a detailed description of the technological principles involved in implementation, reference should be made to an article by Wallace Arden Smith published at pp. 755-766 of IEEE Ultrasonic Symposium, 1989.

The use of composite materials for making piezoelectric ceramics turns out to be advantageous since an acoustic impedance is obtained that is close to the acoustic impedance of biological tissues, and this translates into an increase in the sensitivity of the transducer and to a shorter impulse response. This enables such transducers to be used in medical echographic probes with the advantage of increasing the spatial resolution of such echographic probes.

This manufacturing technology also makes it possible to manufacture complex geometrical shapes, e.g. merely by thermoforming plane elements. Also, the use of a composite makes it possible to achieve transverse coupling that is very low such that the displacement of the sound-emitting surfaces is mainly unidirectional. This contributes to improving the electromechanical coupling and when the transducers are bar-shaped, it limits interactions between them, and this feature is particularly looked-for in echographic probes. It is also possible with composite materials to implement bar type transducers merely by integrating electrodes of the desired shape without cutting up piezoelectric elements.

As a result, composite materials are well-adapted to implementing medical echographic probes and to nondestructive monitoring where requirements are essentially centered on improving electromechanical coupling and spatial resolution for very low emission powers.

Heretofore, it has been believed that composite materials are not suitable for use in therapy (which requires high energy levels) because they suffer from a drop in performance at high excitation levels, as emphasized by Wallace Arden Smith in the above-specified article at p. 758. Mr. Smith emphasizes that at high energy levels transverse coupling increases and the piezoelectric element loses the unidirectional nature of its motion by acquiring transverse deformations that would make it impossible to use bar-type transducers, for example, even in medical echography. Further, firstly because of the increased transverse coupling and secondly because of the addition of polymer material, non-linear behavior of the transducer at high power is suggested.

Under such conditions, the person skilled in the art has had a prejudice against using composite piezoelectric elements for therapeutic treatment by means of ultrasound because high energy levels are required for that purpose.

In contrast, the present inventors have just discovered in a totally unexpected manner that composite piezoelectric elements are strong enough to enable them to emit sufficient energy to achieve therapeutic treatment, be that lithotrity (i.e. by means of a shock wave focused on a focus or target point), or for destroying or treating cells or tissue of a living being by the thermal effect that is obtained from focused ultrasound.

It is recalled here that the energy or power levels required for medical therapy are much greater than those needed for medical imaging. For example, for lithotrity, hyperthermia or tissue removal, the (pulse) energy levels are more than 10,000 times greater than those needed by medical imaging. In terms of power per pulse, these same levels are from 10 times to 1,000 times greater. For example, the energy level that needs to be transmitted for medical imaging is typically less than 1 ten thousandth of a J per pulse. For therapeutic treatment, the energy that needs to be transmitted by the piezoelectric elements is significantly greater than 0.01 J per pulse. For lithotrity the energy level required generally lies in the range 0.01 J per pulse to 1 J per pulse. For medical hyperthermia and for thermal tissue removal, the energy required is generally in the order of several tens of Joules.

SUMMARY OF THE INVENTION

Thus, in a first aspect, the present invention provides the use of at least one composite piezoelectric transducer in the manufacture of an ultrasonic therapy apparatus for applying therapy, in a body zone, in particular to concretions, tissue, or bones, of a living being. Here the term "use" includes a method of treatment or therapy of said living being. This method is defined in the claims which are incorporated herein by reference.

In a particular embodiment, the above-specified composite piezoelectric transducer is a single element of large size.

In another particular embodiment, the emitting surface of the above-specified transducer is split up into a plurality of emitting surfaces capable of being excited separately.

In yet another particular embodiment, a multiplicity of individual composite piezoelectric transducers are used which are assembled together to form a device comprising at least as many emitting surfaces as it has individual transducers. Such a device may be called a "multi-transducer" device.

In another particular embodiment, natural or electronic focusing means are provided for focusing the acoustic or ultrasonic waves emitted by the emitting surfaces of the above-mentioned transducers.

Advantageously, provision may be made for the above-mentioned composite piezoelectric transducers to emit ultrasound waves that are focused on a focal point or "target" point. This focusing may be achieved electronically or naturally by providing the transducer(s) or a multi-transducer device that is physically in the form of a naturally-focusing spherical cup. When electronic focusing is used, the transducers are fed electrically with predetermined phase shifts.

The unexpected effects of using composite piezoelectric ceramic transducers for therapeutic treatment are the following:

even at high energy, it is observed that composite piezoelectric materials exhibit satisfactorily linear behavior; furthermore, given that the composite materials include polymer material, thermal dissipation is less than with conventional ceramic transducers, which would appear, a priori, to prevent them being used in high energy applications, yet it has now been discovered that it is possible to achieve thermal dissipation that is sufficient for enabling therapeutic treatment to be performed; and by using composite technology, it is possible to manufacture multi-transducer devices having a filling factor of close to 100% whereas in conventional technology using a mosaic of ceramic transducers, it is typically not possible to do better than about 66%.

In another particular embodiment of the invention, a mono- or multi-transducer composite piezoelectric device is provided made in the form of a cup that fits substantially over the shape of the body of a patient and the apparatus is caused to emit an essentially spherical wave by phase synthesis introducing phase delays that enable an essentially spherical wave to be synthesized.

At present, a composite piezoelectric transducer which turns out to be particularly advantageous for implementing an acoustic or ultrasonic therapy apparatuses for therapy in particular of concretions, tissue, or bones of a living being, is obtained from sticks of piezoelectric ceramic based on an alloy of zirconate and titanate, in particular an alloy of lead, zirconate and titanate (PZT) included in a compatible polymer matrix selected from the group comprising: an epoxy resin, a silicone and a polyurethane, and preferably an epoxy resin or a polyurethane.

The technology for making composite piezoelectric materials is well known to the person skilled in the art and has been described for the most part in the article by Wallace Arden Smith, published at pp. 755–766 in IEEE Ultrasonic Symposium, 1989.

For example, one of the commonly used techniques is the so-called "dice and fill technique" which consists in starting from a PZT (lead zirconate titanate) type piezoelectric ceramic and in cutting fine grooves in the thickness thereof to form a regular grating of ceramic sticks. The grating is then impregnated with the polymer component which is of the silicone type, the epoxy resin type, or the polyurethane type. Once the resin has polymerized, the material is adjusted to the desired thickness by cutting its base. A grating of independent sticks included in a polymer matrix is then obtained. The following step consists in depositing transducer feed electrodes on each face, e.g. by metal plating in a vacuum. By using masks, it is possible to deposit a single electrode for the entire transducer or a plurality of adjacent electrodes in order to subdivide the transducer assembly into a plurality of groups that can be excited separately. Thereafter, a final polymer layer is deposited which has two functions: electrical insulation and acoustic matching. It is important to ensure that the successive deposits adhere securely to one another. Finally, in a final step, the transducer is shaped to give it an arbitrary shape, e.g. a spherical shape. It should be observed that this operation is sometimes performed before the metal plating stage.

The volume occupied by the piezoelectric material relative to the total volume may lie in the range 8% to 70%. According to the present invention, it is advantageous for the volume proportion of the piezoelectric material relative to the total volume to lie in the range 20% to 40%.

The invention also provides an acoustic or ultrasonic therapy apparatus for applying therapy, in a body zone, in particular to concretions, tissue or bones, of a living being, the apparatus comprising at least one piezoelectric transducer and being characterized in that said piezoelectric transducer is made at least in part of a composite material, the apparatus further including electrical feed means for said transducer enabling it to provide a sufficient dose of acoustic energy to perform said therapy in said body zone. The high level of ultrasonic or acoustic energy that the feed means are capable of sending to said transducer is not less than 0.01 J per pulse during a period of time that is sufficient for performing said therapy, in particular on concretions such as kidney stones, or bile stones, or for treating tissues such as benign or malign tumors, or for treating bones, in particular at fractures or at zones to be treated such as zones of osteoporosis. The invention may also be used for treating varicose veins.

In a variant embodiment, the above-mentioned composite piezoelectric transducer may be disposed outside the body or else it may be mounted on or it may form an integral portion of an endo-cavity probe capable of being inserted into a cavity of the body of a living being.

In another particular variant embodiment of the invention, the above-mentioned composite piezoelectric transducer is used in lithotrity to destroy a stone or "lithiasis" present in the body of a living being by means of a focused sound or ultrasonic wave that forms a shock wave at a focal point.

In another particular variant embodiment, the above-mentioned composite piezoelectric transducer is used to perform medical hyperthermia or thermotherapy or to thermally remove tissue such as tumor tissue by volatilization thereof.

It is possible to provide a multi-transducer composite piezoelectric device for the combined purposes of therapy and of imaging. In a first case, a determined number of transducers enable echographic images to be formed (advantageously by associated electronic means permanently connected thereto) while the other transducers perform the therapeutic function. In a particularly advantageous embodiment, the transducers performing the imaging function may be disposed along one or more emitting lines so as to form one or more image planes that are preferably orthogonal. This disposition is particularly advantageous, in particular because it provides one or more image planes that pass permanently through the focal point when the above-mentioned emitting lines are disposed in a plane of symmetry of the multi-transducer apparatus, thus making it possible to obtain continuous imaging in real time of the therapeutic process.

In a second case, a determined number of the transducers or even all of them provide both an imaging function and a therapeutic function. These two functions may be obtained sequentially by appropriate sequencing control means that are well known to the person skilled in the art.

It should be observed that using composite piezoelectric transducers of the invention in a combined therapy and imaging application is particularly advantageous when associated with the method and device for locating wave focusing as described in Document FR-89 01 628.

Composite piezoelectric transducers of the invention, in particular multi-transducer apparatuses for combined therapy and imaging use, may be applied to ultrasonic hyperthermia treatment of benign or malign tumors of the liver, of the kidney, the prostate, the breast, and also to treatment of varicose veins.

The composite piezoelectric transducer(s) of the invention may advantageously be integrated in an endo-cavity probe, in particular a transrectal probe. In this context, the invention advantageously serves to treat cancer of the prostate.

Such an endo-cavity probe preferably has the structure described in the Applicants' prior patent application FR-91 02 620 filed Mar. 5, 1991, which is incorporated in full herein by reference.

BRIEF DESCRIPTION OF THE DRAWINGS

Other objects, characteristics, and advantages of the invention appear clearly in the light of the following explanatory description made with reference to the presently preferred embodiment of the invention which is given merely by way of example and which does not limit the scope of the invention in any way. In the drawings.

It should be observed that the first transducer numbered 1 (large digit) constitutes, on its own the group number 1 (small digit), with this cup-shaped device constituting the essential portion for emitting focused ultrasonic waves in combination with other essential members shown in FIG. 2.

DETAILED DESCRIPTION

Figure 1:
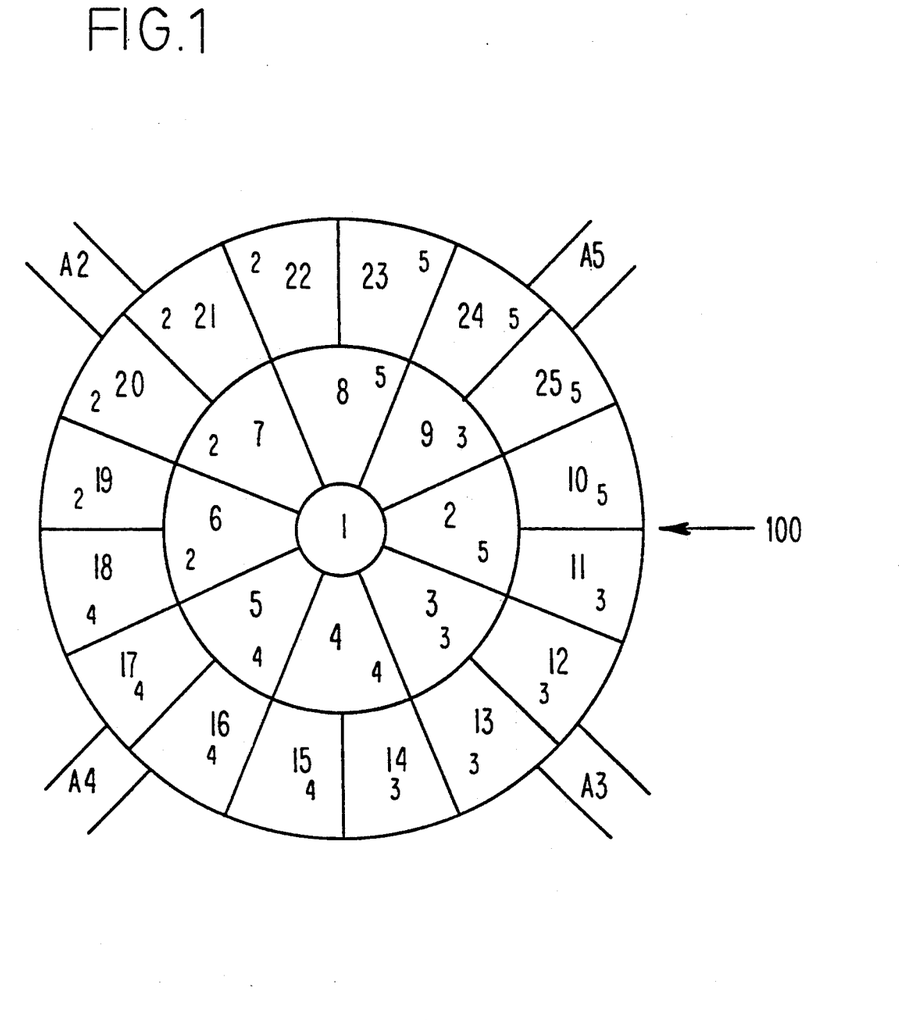
FIG. 1 is a rear view of a spherical focusing cup implemented using a multi-transducer composite piezoelectric apparatus having 25 individual transducers numbered 1 to 25 (large digits) which are subdivided into five distinct groups numbered 1 to 5 (small digits)

The composite multi-transducer device of FIG. 1 is given overall reference numeral 100. The device 100 is made using the method described above. In this particular case, the electrodes are deposited using a mask that defines 25 electrodes that are adjacent and independent and of the shape shown in FIG. 1, thereby forming 25 individual transducers that are capable of being fed separately. The assembly was then shaped to form, in the example, a cup having an opening of 100 mm and a radius of curvature of 160 mm. The piezoelectric material is of the PZT type and it constitutes about 25% of the total volume. The 25 transducers respectively numbered 1 to 25 (large digits) are subdivided into five subgroups numbered 1 to 5 (small digits) which are fed in groups and individually as described below with reference to FIG. 2. The feeds to the groups 2, 3, 4, and 5 are deposited on the sides and are referenced $A_2$, $A_3$, $A_4$, and $A_5$ respectively.

The transducer 1 constitutes a group on its own, and for practical reasons it is combined with group No. 2 to be fed from feed $A_2$.

Figure 2:
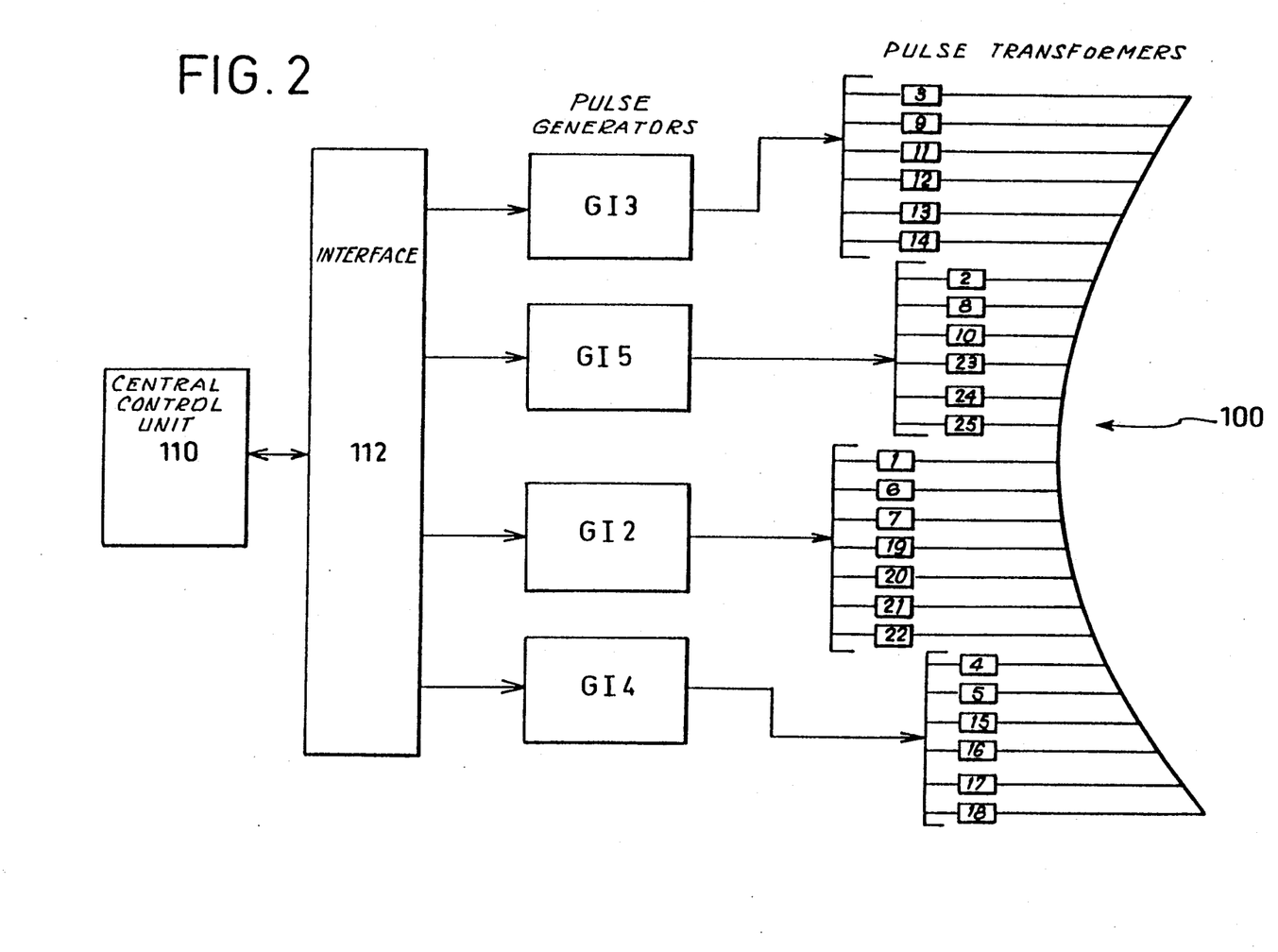
FIG. 2 is a block diagram of an acoustic or ultrasonic therapeutic apparatuses of the present invention for applying therapy to tissue of a living being and constituting an application of the FIG. 1 multi-transducer apparatus having composite type transducers.

The technique for making the multi-transducer composite device is conventional and as described by Wallace Arden Smith at pp. 755–766 of IEEE Ultrasonic Symposium, 1989, and in particular with reference to FIG. 2.

Accompanying FIG. 2 shows a block diagram of the cup-shaped multi-transducer device 100 of FIG. 1 together with its electronic feeds. It can be seen that each individual composite piezoelectric transducer of the device 100 is associated with a pulse transformer which is given the same reference numeral as the number of the individual transducer that it feeds.

There are therefore as many pulse transformers as there are transducers in the cup.

Thus, in this case, there are 25 pulse transformers which are grouped together to form four groups fed by four pulse generators. In this case, the four main groups 2, 3, 4, and 5 are shown together with their associated pulse generators referenced G12, G13, G14, and G15. These pulse generators are controlled by a central control unit 110, e.g. in the form of a computer and which contains, in the form of a file, all of the information necessary for individually controlling each of the 25 individual transducers. This is done by attributing control parameters to the transducers of the various electronic paths, and in particular phase delays and firing management, e.g. with respect to the number of shots and to the firing rate. This data is sent by the central control unit 110 to the pulse generator cards which are referred to as "pulse generators" via an interface card 112, as shown in FIG. 2.

Each pulse generator card can control six to seven transducers independently. It is therefore necessary in this case to provide at least four cards, given that the central transducer 1 which constitutes a group on its own is controlled by the pulse generator referenced G12.

It will be understood that the pulses which are sent by the pulse generators are received by the pulse transformers for amplification and are transmitted to the transducers individually, thereby providing a high degree of flexibility in operation and making it possible to adjust the overall power of the multi-transducer composite piezoelectric device 100 at will.

The central individual piezoelectric element referenced 1 in FIG. 1 has been used to perform tests on the linearity of the sensitivity of the transducer element in terms of positive pressure P+ as a function of the applied voltage.

Figure 3:
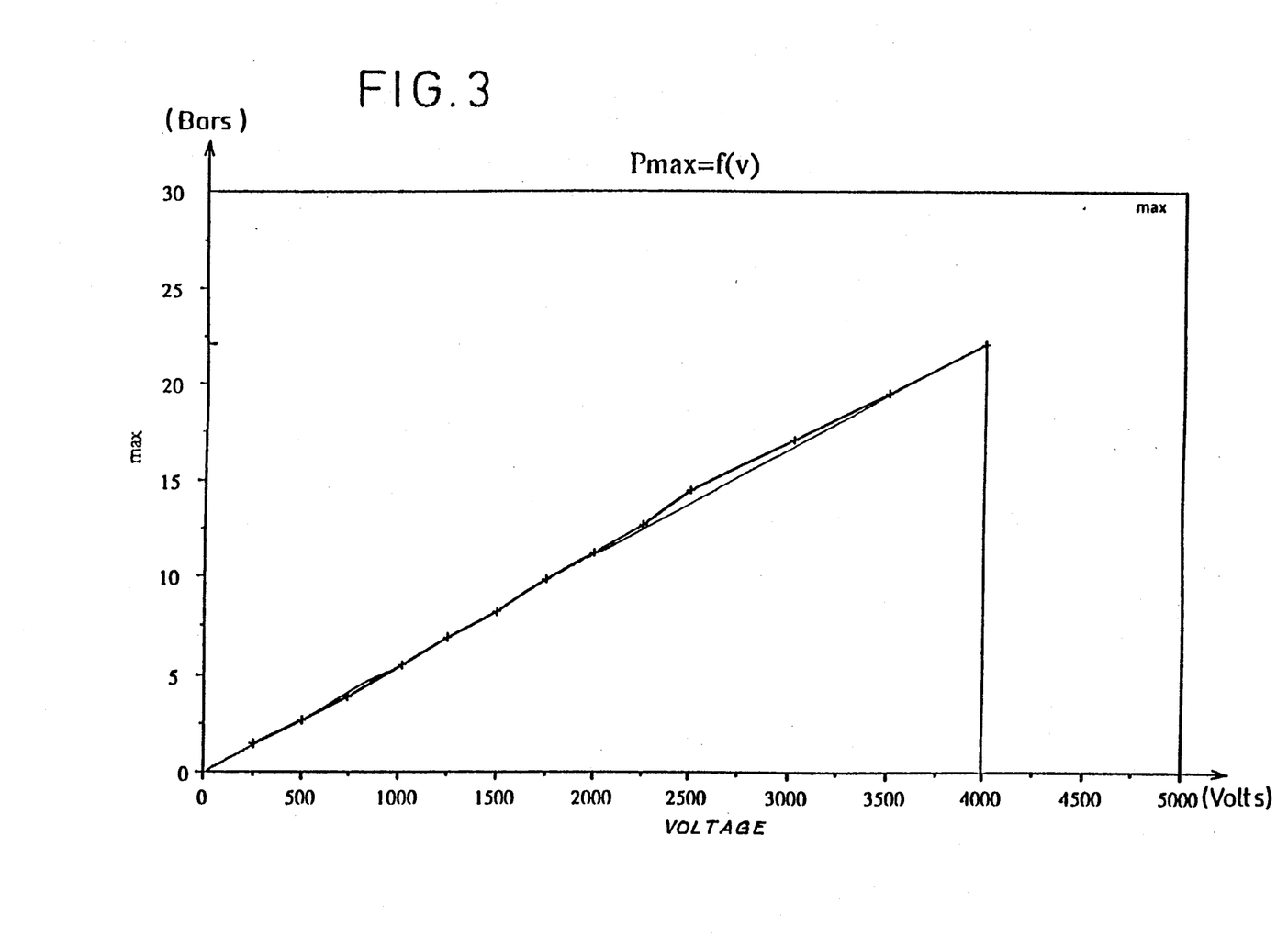
FIG. 3 is a graph showing the linearity obtained with the central composite piezoelectric transducer number 1 (large digit) constituting the first group in FIG. 1; the maximum pressure obtained in bars is plotted up the Y-axis as a function of the applied voltage expressed in volts.

The results of these tests are given in the form of curves in FIG. 3 where volts are plotted along the X-axis and pressure in bars is plotted up the Y-axis giving the maximum pressure obtained as a function of the applied voltage. The resulting curve has a slope of 5.6 mbars/volt, which is remarkable.

It is also surprising to observe that this curve is extremely linear regardless of the applied voltage and the pressure of the waves emitted to the focal point at the center of the cup, expressed in bars.

Figure 4:
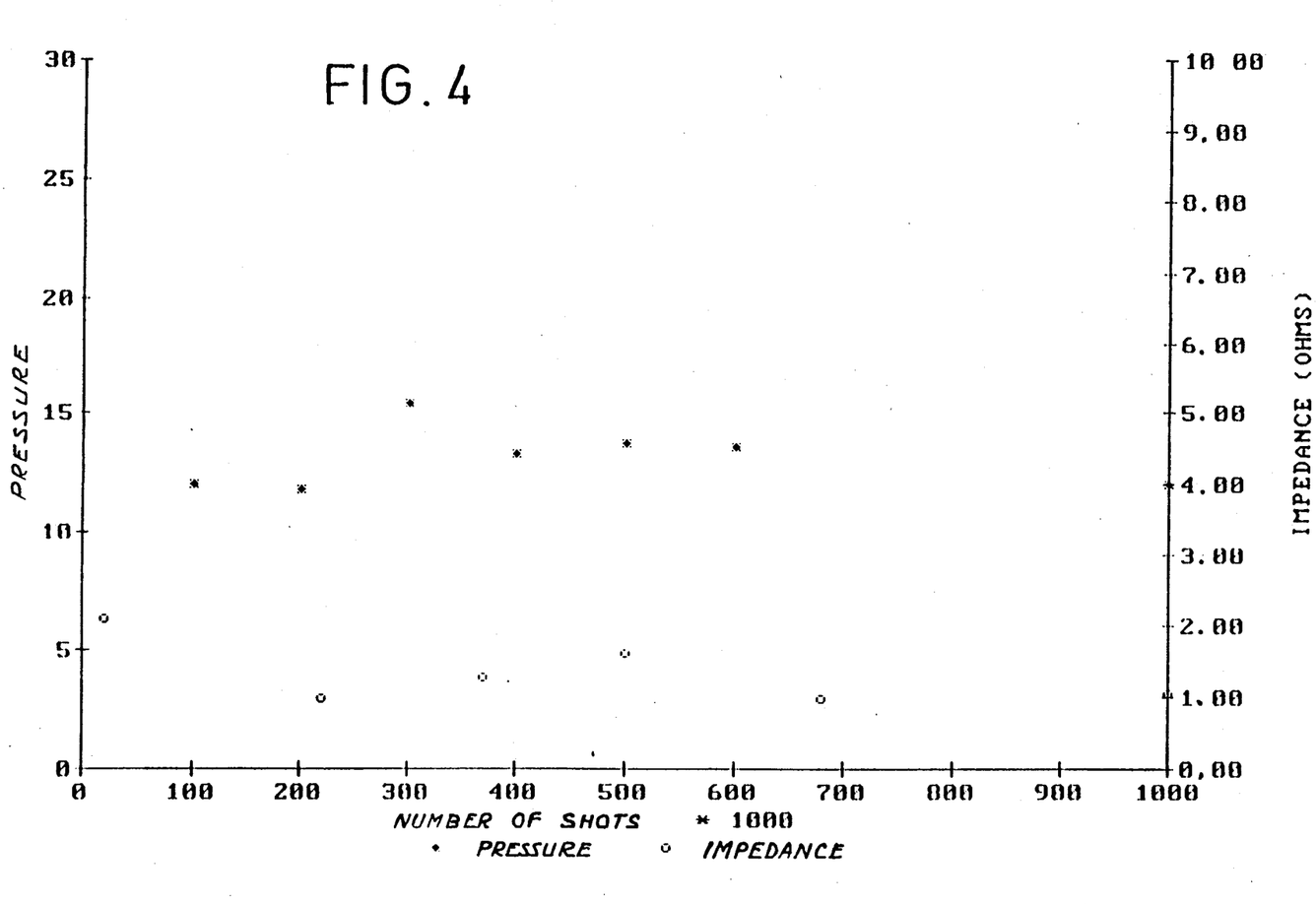
FIG. 4 is a graph showing the aging of the number 1 composite piezoelectric transducer of FIG. 1 as obtained at a given pressure expressed in bars and plotted up the Y-axis as a function of the number of shots multiplied by 1,000 plotted along the X-axis (curve plotted with asterisks at \*-\*), and secondly the impedance in ohms plotted up the righthand Y-axis as a function of the number of shots multiplied by 1,000 plotted along the X-axis (curve o-o)

In addition, aging tests have also been performed using the composite piezoelectric transducer 1 of FIG. 1, with these tests being shown in the form of a curve in FIG. 4 where number of shots X 1,000 is plotted along the X-axis and where the lefthand Y-axis indicates pressure in bars. The curve showing pressure as a function of shots is plotted with asterisks *. The righthand Y-axis gives impedance in ohms and the corresponding curve is plotted using small circles o.

It can be seen that at an initial pressure of about 13 bars, this can be maintained essentially constant regardless of the number of shots, which is quite remarkable.

Similarly, the impedance of the composite piezoelectric material is kept essentially constant at around 1 ohm regardless of the number of shots, which is likewise remarkable and unexpected for the person skilled in the art.

The invention thus makes it possible to achieve all of the above-announced determining technical advantages.

In particular, the composite piezoelectric transducer of the invention, in particular when in the form of a multi-transducer device, can be used for making an acoustic or an ultrasonic therapy apparatus for therapy that may be destroying a concretion, destroying tissue such as a tumor, or treating bones.

Figure 5:
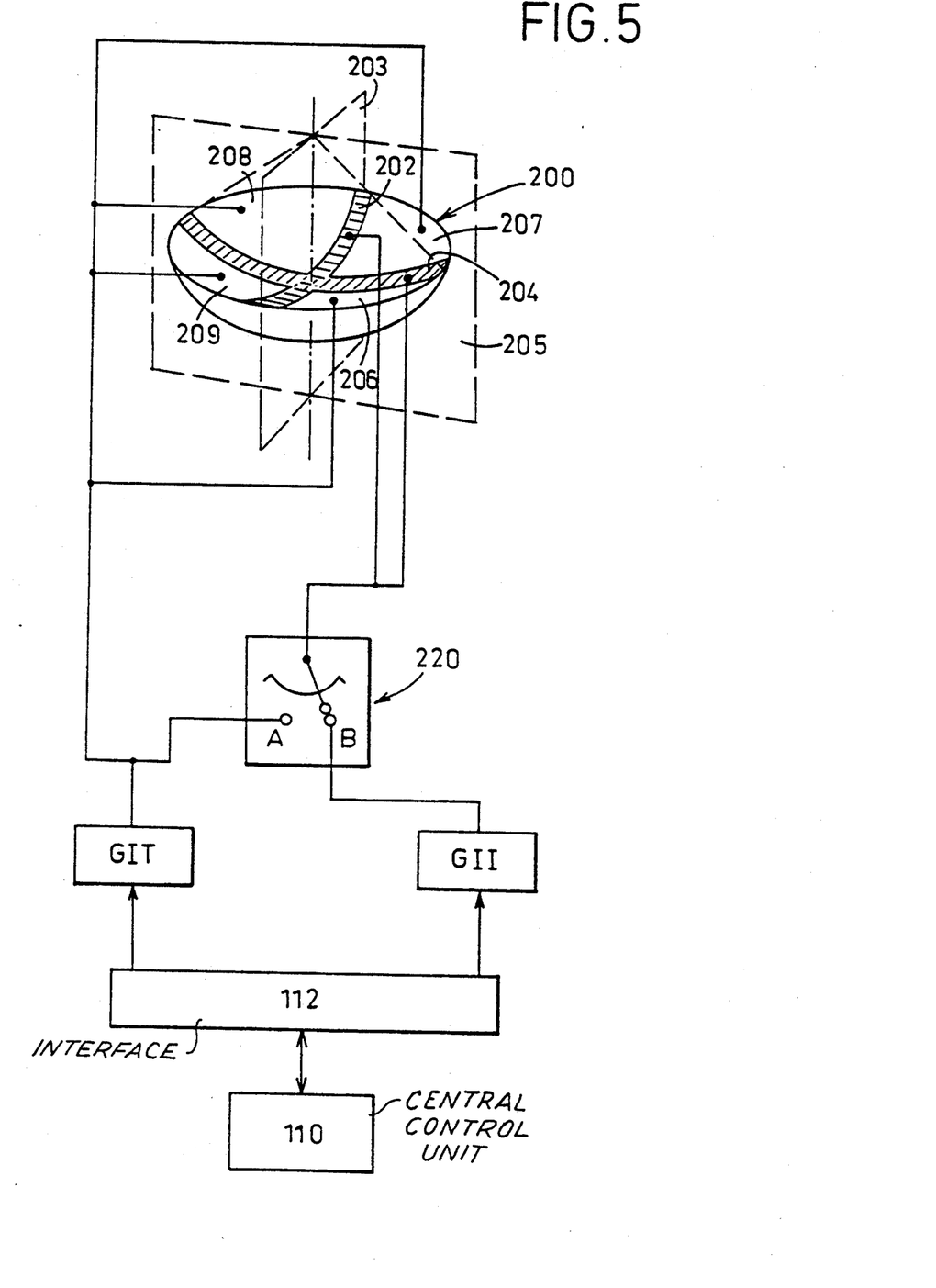
FIG. 5 is a diagram showing a second embodiment of an acoustic or ultrasonic therapy apparatus performing both imaging and therapy.

With reference to FIG. 5, there can be seen a second embodiment of therapy apparatus of the present invention which has combined therapy and imaging functions, comprising a multi-transducer device of a type similar to that shown with reference to FIGS. 1 and 2, in the form of a cup, but in which a plurality of transducers associated with an imaging function are disposed, in this case in two perpendicular lines 202 and 204 occupying planes of symmetry of the cup 200, thereby obtaining image planes 203 and 205 that permanently contain the focal point F or center of the naturally-focusing spherically-shaped cup 200.

In addition, the other transducers of the cup 200 are distributed over four preferential sectors respectively referenced 206, 207, 208, and 209 and which perform a therapy function.

In this case also, there is a central control unit 110, e.g. a computer, controlling (via an interface 112) therapy pulse generators (GIT) or an imaging pulse generator (GII) respectively connected to the sectors of therapy transducers 206, 207, 208, and 209, or to the imaging transducers disposed on the lines 202 and 204 which are disposed orthogonally in this case. In a particularly preferred variant, a switch device 220 is included having a position A and a position B. When the switch is in its position A, the therapy pulse generator also causes the transducers in the imaging lines 202 and 204 to generate therapy pulses, i.e. when the switch is in position A, all of the transducers in the cup perform therapy, i.e. they operate at high power. In contrast, when the switch is in its position B, as shown in FIG. 5, the therapy pulse generator controls the transducers in the therapy sectors 206, 207, 208, and 209 only, while the imaging pulse generator GII controls the transducers disposed in the emitting lines 202 and 204 for imaging purposes so as to construct an echographic image of the region around the focus F occupying two perpendicular planes each including the point F.

It will easily be understood that with the apparatus as shown in FIG. 5, it is possible by appropriate programming of the interface 112 by the control unit 110 when the switch is in position A to make the pulse generators operate therapeutically to provide a sequence of therapy pulses per se controlling all of the transducers in the cup 200, or else under reduced power in an imaging mode to control all of the transducers in the cup 200 at an imaging power. The apparatus thus provides most appreciable versatility in use.

The invention thus covers all means constituting technical equivalants to the means described and various combinations thereof.

It should be observed that all of the elements of the embodiments described with reference to FIGS. 1 to 5 form an integral portion of the invention and thus of the present description. The invention also covers any characteristic that appears to be novel over any of the prior art.

The composite piezoelectric transducer of the invention can be used to perform medical hyperthermia or thermotherapy, or to damage tissue thermally, e.g. tumor tissue or varicose tissue, by causing a thermal effect selected from coagulation, necrosis, and volatilization thereof.

What is claimed is:

1. A method for effecting therapeutic treatment of a body zone, comprising: providing at least one composite piezoelectric transducer element for emitting ultrasound waves, wherein said composite transducer element comprises piezoelectric ceramic material in combination with a polymer; and applying a current to said composite piezoelectric transducer element for causing said piezoelectric transducer element to emit ultrasound waves having sufficient acoustic energy for effecting said therapeutic treatment of said body zone.

2. The method of claim 1, further comprising the steps of focusing said ultrasound waves emitted by said piezoelectric transducer element to a focus, and bringing said body zone into coincidence with said focus for effecting said therapeutic treatment.

3. The method of claim 2, wherein said step of providing at least one composite piezoelectric transducer element comprises providing a plurality of composite piezoelectric transducer elements.

4. The method of claim 3, wherein said step of focusing said ultrasound waves comprises orienting said plurality of composite piezoelectric transducer elements such that their respective emitted ultrasound waves coincide at said focus.

5. The method of claim 3, wherein said step of focusing said ultrasound waves comprises applying current to said plurality of composite piezoelectric transducer elements with predetermined phase shifts.

6. The method of claim 3, wherein said step of applying a current to said plurality of composite piezoelectric transducer elements comprises applying a sufficient current for generating an energy greater than 0.01 joule per pulse.

7. The method of claim, wherein said step of applying a current comprises applying a current for effecting one of lithotrity, hyperthermia and tissue removal.

8. The method of claim 3, further comprising the step of using at least a first piezoelectric transducer element for effecting imaging of said body zone.

9. The method of claim 8, further comprising the step of selectively applying said current to said at least a first piezoelectric transducer element for effecting imaging of said body zone.

10. The method of claim 3, wherein said step of applying a current comprises applying a current for effecting one of lithotrity, hyperthermia and tissue removal.

11. The method of claim 1, wherein said step of applying a current to said at least one composite piezoelectric transducer element comprises applying a sufficient current for generating an energy greater than 0.01 joule per pulse.

12. The method of claim 1, wherein said step of applying a current comprises applying a current for effecting one of lithotrity, hyperthermia and tissue removal.

13. An apparatus for effecting therapeutic treatment of a body zone, comprising:
 at least one composite piezoelectric transducer element for emitting ultrasound waves, wherein said composite transducer element comprises piezoelectric ceramic material in combination with a polymer; and
 means for applying a current to said composite piezoelectric transducer element for causing said piezoelectric transducer element to emit ultrasound waves having sufficient acoustic energy for effecting said therapeutic treatment of said body zone.

14. The apparatus of claim 13, further comprising means for focusing said ultrasound waves emitted by said piezoelectric transducer element to a focus, whereby said body zone may be brought into coincidence with said focus for effecting said therapeutic treatment.

15. The apparatus of claim 14, wherein said at least one composite piezoelectric transducer element comprises a plurality of composite piezoelectric transducer elements.

16. The apparatus of claim 15, wherein said means for focusing said ultrasound waves comprises means for orienting said plurality of composite piezoelectric transducer elements such that their respective emitted ultrasound waves coincide at said focus.

17. The apparatus of claim 15, wherein said means for focusing said ultrasound waves comprises means for applying current to said plurality of composite piezoelectric transducer elements with predetermined phase shifts.

18. The apparatus of claim 15, wherein said means for applying a current to said plurality of composite piezoelectric transducer elements comprises means for applying a sufficient current for generating an energy greater than 0.01 joule per pulse.

19. The apparatus of claim 18, wherein said means for applying a current comprises means for applying a current for generating sufficient energy for effecting one of lithotrity, hyperthermia and tissue removal.

20. The apparatus of claim 15, wherein at least a first piezoelectric transducer element is useable for effecting imaging of said body zone and further comprises, means for selectively applying said current to said at least a first piezoelectric transducer element 4 effecting imaging of said body zone.

21. The apparatus of claim 15, wherein said means for applying a current comprises means for applying a current for generating sufficient energy for effecting one of lithotrity, hyperthermia and tissue removal.

22. The apparatus of claim 13, wherein said means for applying a current to said at least one composite piezoelectric transducer element comprises means for applying a sufficient current for generating a energy greater than 0.01 joule per pulse.

23. The apparatus of claim 13, wherein said means for applying a current comprises means for applying a current for generating sufficient energy for effecting one of lithotrity, hyperthermia and tissue removal.

* * * * *